United States Patent [19]

Summers et al.

[11] Patent Number: 5,611,690
[45] Date of Patent: Mar. 18, 1997

[54] METHOD AND APPARATUS FOR SPRAYED DELIVERY OF TOOTH BLEACHING AGENT

[75] Inventors: Georgene Summers; Mitchell A. Rothstein, both of New York, N.Y.

[73] Assignee: E. Mishan & Sons, Inc., New York, N.Y.

[21] Appl. No.: 631,604

[22] Filed: Apr. 2, 1996

[51] Int. Cl.$^6$ ............................................ A61C 5/04
[52] U.S. Cl. ........................................ 433/215; 433/89
[58] Field of Search ............................. 433/216, 215, 433/80, 88, 89

[56] References Cited

U.S. PATENT DOCUMENTS

| | | | |
|---|---|---|---|
| Re. 14,961 | 10/1920 | Rhein . | |
| Re. 34,196 | 3/1993 | Munro | 433/215 |
| 1,642,653 | 9/1927 | Goldstein . | |
| 2,601,238 | 6/1952 | Bell | 167/93 |
| 2,622,058 | 12/1952 | Kesel | 167/93 |
| 3,624,219 | 11/1971 | Perlitsh | 424/7 |
| 4,032,627 | 6/1977 | Suchan et al. | 424/54 |
| 4,060,600 | 11/1977 | Vit | 424/53 |
| 4,127,645 | 11/1978 | Witzel et al. | 424/44 |
| 4,267,166 | 5/1981 | Yajima | 424/48 |
| 4,574,081 | 3/1986 | Shymon | 424/52 |
| 4,663,154 | 5/1987 | Ryan | 424/54 |
| 4,741,700 | 5/1988 | Barabe | 433/229 |
| 4,919,918 | 4/1990 | Cole et al. | 424/44 |
| 4,971,785 | 11/1990 | Wilson et al. | 424/44 |
| 5,009,885 | 4/1991 | Yarborough | 424/53 |
| 5,032,178 | 7/1991 | Cornell | 106/35 |
| 5,057,308 | 10/1991 | Hill et al. | 24/52 |
| 5,057,309 | 10/1991 | Hill et al. | 424/52 |
| 5,076,791 | 12/1991 | Madray, Jr. | 433/215 |
| 5,084,268 | 1/1992 | Thaler | 424/53 |
| 5,098,303 | 3/1992 | Fischer | 433/215 |
| 5,145,664 | 9/1992 | Thompson | 424/49 |
| 5,165,424 | 11/1992 | Silverman | 128/861 |
| 5,171,564 | 12/1992 | Nathoo et al. | 424/53 |
| 5,234,342 | 8/1993 | Fischer | 433/215 |
| 5,376,006 | 12/1994 | Fischer | 433/215 |
| 5,392,947 | 2/1995 | Gentile | 220/665 |
| 5,427,768 | 6/1995 | Tung | 424/52 |
| 5,427,770 | 6/1995 | Viccaro et al. | 424/54 |
| 5,460,527 | 10/1995 | Kittelsen | 433/215 |
| 5,476,647 | 12/1995 | Chow et al. | 424/52 |
| 5,496,541 | 3/1996 | Cutler | 424/50 |
| 5,500,207 | 3/1996 | Goulet | 424/54 |

*Primary Examiner*—Jeffrey A. Smith
*Attorney, Agent, or Firm*—Notaro & Michalos PC

[57] ABSTRACT

An apparatus for and method of whitening teeth utilizes a liquid composition containing a liquid tooth whitening bleach and a breath freshener. The composition is sprayed onto the teeth and is allowed to stay on the teeth for a short period of time. The composition is then expectorated. The process is repeated two to four times a day. The apparatus of the invention comprises a small, compact and portable container with spraying mechanism which contains a supply of the composition and which can be used both in the home and outside for convenience and economy.

14 Claims, 1 Drawing Sheet

METHOD AND APPARATUS FOR SPRAYED DELIVERY OF TOOTH BLEACHING AGENT

CROSS REFERENCE TO RELATED APPLICATION

The present application claims domestic priority benefits on a provisional application, filed Sep. 12, 1995, with Provisional Application No. 60/003590 and titled:

A Method of Delivering a Tooth Bleaching Agent in Liquid Form Together With a Breath Freshener, wherein the Active and Inactive Ingredients are Placed Onto the Teeth by Use of a Portable Aluminum/Plastic Tube With a Non-Aerosol Spray Pump.

FIELD AND BACKGROUND OF THE INVENTION

No convenient and inexpensive way is known for whitening teeth. There is also no known combination of a tooth whitener and a breath freshener, in an easy-to-use applicator.

Currently there are three known approaches for whitening teeth.

In one approach, a bleaching gel is placed into one or two mouth trays. The user sinks his or her teeth into the tray, thereby covering the teeth with the gel. It is common to keep the teeth in contact with the gel for a period of two to eight hours. Since the whitening gel often includes a whitening agent containing 10%–12% active ingredient, this technique, commonly leads to gum irritation.

A second known technique utilizes a three-step process. In the first step, the user holds a liquid cleaning composition in the mouth for approximately one minute. After this, a bleaching gel is applied to the teeth using, for example, a cotton swab. The gel is left on the teeth for approximately three minutes. This is followed by brushing, using an abrasive tooth polish.

The third technique utilizes an abrasive "whitening" tooth paste, which is brushed directly onto the teeth using a toothbrush, in the same way that conventional tooth paste is utilized.

In the field of breath freshening compositions and techniques, it is known to spray a breath freshener into the mouth, in particular, using a small compact pump bottle or aerosol spray container. It is also known to freshen the breath using small mints, mouthwash, chewing gum, breath freshening drops, breath gel caps which are swallowed and a wide variety of other techniques and products.

SUMMARY OF THE INVENTION

The present invention is a non-invasive and customer-friendly method and apparatus for whitening the teeth and freshening the breath. According to the present invention, both functions are achieved more effectively, more economically and in a safer manner. A small, portable applicator, in the form of a pump bottle, receives the liquid composition containing tooth whitener and breath freshener. To use the product, the user opens his or her mouth and exposes the teeth. The composition is sprayed onto the teeth and then the mouth is closed, leaving the composition on the teeth for approximately 30 to 45 seconds. The composition is then expectorated. This process is repeated two or three times a day.

The invention does not utilize unsightly and uncomfortable trays nor is it subject to the irritation that is common when utilizing tooth whitening gels in such trays. A person can utilize the present invention in less than five minutes a day and in a convenient and inexpensive manner to achieve the desired results.

The present invention also does not utilize abrasive compositions which may damage tooth enamel. The present invention can be utilized in the home or outside the home with equal facility. The product is portable and can be carried anywhere. The person can also see immediate results and the invention has the additional advantage of freshening the breath while whitening the teeth in one easy process. The invention is also safer in that the composition is only momentarily held in the mouth and not maintained in contact with the teeth and sensitive gums for long periods as is common with some prior art techniques.

This also reduces the tendency for the person to ingest the bleaching composition, which can hardly be avoided when using bleaching gels that are maintained in contact with the teeth for many hours.

Accordingly, a further object of the present invention is to provide a method for whitening teeth comprising storing a composition containing a tooth whitening bleach in a spraying container having a spraying mechanism for spraying the composition out of the container, activating the mechanism to spray the composition onto the teeth, and allowing the composition to remain on the teeth for a selected period of time.

Another object of the invention is to include a breath freshener as part of the composition.

A still further object of the invention is to provide an apparatus for whitening teeth comprising a container, a composition in the container, the composition containing a tooth whitening bleach alone or in combination with a breath freshener, and a spraying mechanism for spraying the composition out of the container for use on the teeth.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENT

Figure 1:
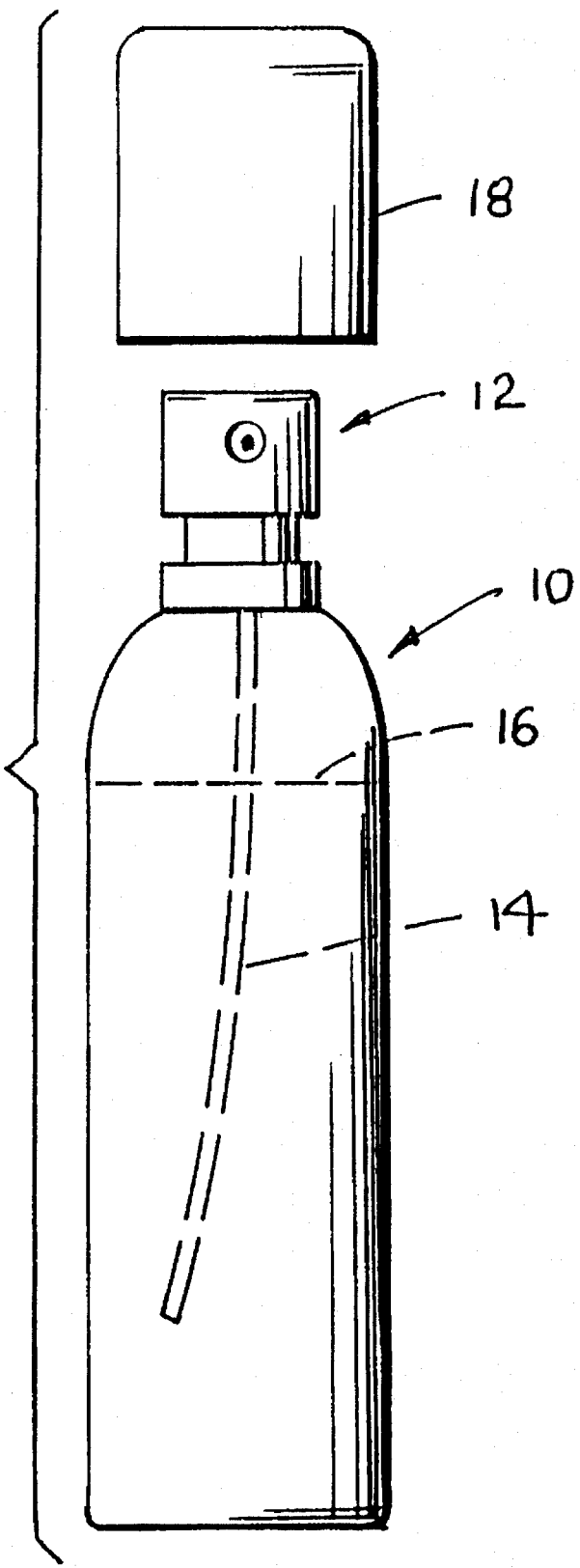
FIG. 1 is an exploded side elevational view of an apparatus of the present invention.

Referring to the drawing in particular, the invention embodied in FIG. 1 comprises a spraying container generally designated 10 made, for example, of aluminum or plastic. The container has an upper opening which is closed by a spraying mechanism generally designated 12. Mechanism 12 is of conventional design and, for example, includes a syphon hose 14 which extends down into the interior of container 10 and a blunt pump head or actuator button. Container 10 contains a liquid composition filled to a level 16. The composition contains a tooth whitening bleach alone or, in a preferred embodiment of the invention, a combination of liquid tooth whitening bleach and liquid breath freshener. A metal or plastic cap 18 is detachably engagable over the spraying mechanism 12 and with the container 10 to complete the small compact structure that can be carried for use outside the home, or stored in a medicine cabinet or the like, for use in the home. Advantageously, the container with cap is approximately 1½" to 6" tall, although smaller or larger containers can be utilized.

An important advantage of the invention is the portability and compactness of the apparatus which increases the chances that the consumer will actually use the invention in a continuing program. The lack of unsightly and difficult to use apparatus such as the use of bleaching gels and mouth trays also increases the chance that the person will follow through with the treatment and achieve whitening of the teeth.

A clinical study was conducted to verify the usefulness the present invention.

The composition utilized for that study contained the following ingredients:

| Ingredients | Approximate Amounts (wt %) |
|---|---|
| Deionized Water | 67 |
| Glycerine | 10 |
| Polysorbate 20 | 2 |
| Propylene Glycol | 7 |
| Hydrogen Peroxide | 2 |
| Sodium Fluoride | 2 |
| Sodium Saccharin | 1 |
| Aspartame | 1 |
| Phenacetin | 1 |
| Flavor/s (Peppermint Oil/Cinnamon/Wintergreen) | 5 |
| Methylparaben | 1 |
| Disodium EDTA | 1 |

The test group included 50 individuals both male and female, ages 18–77 who were displeased with the way their teeth appeared. Many of the individuals had previously used other whitening products such as gels or whitening toothpastes, and had ceased using those products because they were time consuming, expensive and cumbersome. The individuals in the group used the method of the invention and reported continued use of the invention because of its convenience, flexibility of use, low cost, portability, lack of messy application, and its dual purpose (both tooth whitening and breath freshening).

Each individual was instructed to practice the invention by first opening the mouth and exposing the teeth, for example, by clenching the teeth with the lips open. The next step is spraying the composition onto the tooth surfaces, followed by closing the lips and maintaining the spray on the teeth for a period of 30–45 seconds. The individuals were instructed to then expectorate (spit the composition from the mouth). The individuals were instructed to repeat this process two to three times a day. After 30 days, the individuals reported having whiter teeth.

In the alternate composition 2 wt % urea peroxide replaces the hydrogen peroxide. Due to the stronger taste, the flavoring is increased to 7 wt % and the amount of water is reduced to 65%. The fluoride ingredient also increases the usefulness of the invention in providing a fluoride treatment while freshening the breath and whitening the teeth.

While a specific embodiment of the invention has been shown and described in detail to illustrate the application of the principles of the invention, it will be understood that the invention may be embodied otherwise without departing from such principles.

What is claimed is:

1. A method for whitening teeth, comprising:

storing a liquid composition containing a tooth whitening bleach and a breath freshener in a portable spraying container having a spraying mechanism with a blunt actuator button for spraying the composition out of the container;

exposing surfaces of the teeth by opening the mouth and exposing the teeth of a person whose teeth are to be whitened;

activating the spraying mechanism by pressing the actuator button to spray the composition out of the container;

directing the sprayed composition onto the exposed surfaces of the teeth;

allowing the composition to remain on the teeth for a selected short period of time; and thereafter expectorating the composition.

2. A method according to claim 1, including repeating the steps of directing the spray onto the teeth and allowing the composition to remain on the teeth for the selected period of time, from two to four times daily.

3. A method according to claim 2, wherein the selected period of time is from about 30 to about 45 seconds.

4. A method according to claim 3, wherein the spray container is cylindrical and is about 1-½ to 6" tall.

5. A method according to claim 2, including the liquid composition also containing, in addition to the tooth whitening bleach and breath freshener, flavoring, deionized water, glycerine and propylene glycol.

6. A method according to claim 5, wherein the tooth whitening bleach is selected from the group consisting of hydrogen peroxide and urea peroxide.

7. A method according to claim 1, wherein the selected period of time is from about 30 to about 45 seconds.

8. A method according to claim 1, wherein the portable spray container is cylindrical and is about 1-½ to 6" tall.

9. A method according to claim 1, including the liquid composition also containing, in addition to the tooth whitening bleach and breath freshener, flavoring, deionized water, glycerine and propylene glycol.

10. A method according to claim 9, wherein the tooth whitening bleach is selected from the group consisting of hydrogen peroxide and urea peroxide.

11. An apparatus for whitening teeth, comprising:

a spraying container;

a spraying mechanism connected to the spraying container for spraying liquid from the spraying container, the spraying mechanism having a blunt actuator button for spraying exposed surfaces of the teeth;

a liquid composition at least partly filling the spraying container, the composition containing a tooth whitening bleach and a breath freshener.

12. An apparatus according to claim 11, wherein the liquid composition includes deionized water, glycerine, propylene glycol, and flavoring.

13. An apparatus according to claim 11, wherein the composition includes fluoride.

14. An apparatus according to claim 11, wherein the whitening bleach is urea peroxide or hydrogen peroxide.

* * * * *